United States Patent [19]

Plummer

[11] 4,214,004
[45] * Jul. 22, 1980

[54] INSECTICIDAL CYCLOPROPANECARBOXYLATES FROM SUBSTITUTED [1,1'-BIPHENYL]-3-YLMETHYL COMPOUNDS

[75] Inventor: Ernest L. Plummer, North Tonawanda, N.Y.

[73] Assignee: FMC Corporation, Philadelphia, Pa.

[*] Notice: The portion of the term of this patent subsequent to Dec. 21, 1995, has been disclaimed.

[21] Appl. No.: 966,405

[22] Filed: Dec. 4, 1978

[51] Int. Cl.$^2$ .................. C07C 69/74; A01N 9/30
[52] U.S. Cl. ............................ 424/305; 560/124; 568/642; 568/643; 568/807; 260/649 DP
[58] Field of Search .................. 560/124; 424/305

[56] References Cited

U.S. PATENT DOCUMENTS

| | | | |
|---|---|---|---|
| 4,024,163 | 5/1977 | Elliot | 560/124 |
| 4,130,657 | 12/1978 | Plummer | 560/124 |

FOREIGN PATENT DOCUMENTS 1401279 7/1975 United Kingdom.

OTHER PUBLICATIONS

Elliott, Bull. Wld. Hlth. Org., 44, p. 315 (1970).
Elliott, "Synthetic Pyrethroids", American Chemical Soc., Washington, D.C., 1977, pp. 1-28.
Farkas, Coll. Czech. Chem. Comm., 24, p. 2230 (1959).
Itaya, Chem. Abst. 72, 121192, (1970).
Matsuo, Agr. Biol. Chem., 40, p. 247 (1976).
Sawada, Bull. Chem. Soc. Jap., 45, p. 1206 (1972).

Primary Examiner—Norman Morgenstern
Assistant Examiner—Michael Shippen
Attorney, Agent, or Firm—Richard L. Hansen; Henry R. Ertelt

[57] ABSTRACT

Substituted [1,1'-biphenyl]-3-ylmethyl 3-(2,2-dihaloethenyl)-2,2-dimethylcyclopropanecarboxylates, as well as processes, uses, and intermediates thereto, are disclosed. The substituted [1,1'-biphenyl]-3-ylmethyl 3-(2,2-dihaloethenyl)-2,2-dimethylcyclopropanecarboxylates control a broad spectrum of insects as well as acarids.

17 Claims, No Drawings

INSECTICIDAL CYCLOPROPANECARBOXYLATES FROM SUBSTITUTED [1,1'-BIPHENYL]-3-YLMETHYL COMPOUNDS

This invention pertains to the field of bioaffecting compositions; more specifically, it pertains to novel carboxylic acid esters which are pyrethroid insecticides, processes and intermediates thereto, insecticidal and acaricidal compositions containing the novel esters, and to the use of the compositions for controlling insects and acarids.

Pyrethrins have long been of interest as insecticides. Ever since it was discovered that pyrethrins are organic esters, various synthetic modifications have been made in the carboxylic acid and in the alcohol moieties on either side of the ester linkage. Many of the synthetic pyrethroids are more effective than the natural pyrethrins, and recent modifications have overcome a chronic pyrethrin problem—instability to air and light.

The carboxylic acid moiety in the aforesaid esters is often a 2,2-dimethylcyclopropane-1-carboxylic acid with various substituents in the 3-position. A class of pyrethroids of current commercial interest contains the 2,2-dihaloethenyl group in the 3-position; for example, pyrethroids containing the 3-(2,2-dichloroethenyl) and 3-(2,2-dibromoethenyl)-2,2-dimethylcyclopropanecarboxylic acid units are disclosed in Elliott, et al., U.S. Pat. No. 4,024,163.

Many variations in the alcohol moiety of the aforesaid esters have been disclosed also. The alcohols appearing in the most active pyrethroids of current commercial interest are well-known in the prior art and are described by the structural formula

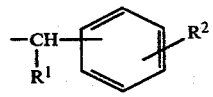

wherein $R^1$ is a hydrogen atom, an alkynyl group, a methyl group, or a cyano group; and $R^2$ is a phenoxy group, a benzyl group, or a phenylthio group. Representative alcohols are 3-phenoxybenzyl alcohol and α-cyano-3-phenoxybenzyl alcohol.

According to M. Elliott, Bull. Wld. Hlth. Org., 44, 315 (1970), it is "essential for powerful pyrethrinlike activity" that the alcohol moiety, represented by HO—[—C-D-E-F], contain certain structural units. It is necessary that the unit C be a tetrahedral carbon atom chemically bonded, not only to the alcoholic oxygen atom O, but to unit D, the remainder of a cyclopentenolone ring, a benzene or furan ring, or C≡C, so that "the carbon atoms in C, D, and E are coplanar". "The unit E is —CH₂—, —O—, or —CO—, or a sterically equivalent link, such that an unsaturated centre F (an olefinic or acetylenic bond, a conjugated system of double bonds, or an aromatic ring) can adopt a position skew to the direction defined by C, D, and E." The alcohol moieties in the most active of the pyrethroid esters of current commercial interest all contain a linking unit E, for example, —O— in the representative alcohols named above. Copending U.S. patent application Ser. No. 844,099, filed Oct. 20, 1977, now U.S. Pat. No. 4,130,657, discloses that the linking unit E is not required, and [1,1'-biphenyl]-3-ylmethyl 3-(2,2-dihaloethenyl)-2,2-dimethylcyclopropanecarboxylates, wherein the halogen is chlorine or bromine, exhibit insecticidal and acaricidal activity.

It has now been found that [1,1'-biphenyl]-3-ylmethyl 3-(2,2-dihaloethenyl)-2,2-dimethylcyclopropanecarboxylates having substituent groups selected from halo, haloalkyl, lower alkyl, lower alkoxy, and nitro on the benzene rings of the biphenyl unit also exhibit pronounced insecticidal and acaricidal activity, activity which is especially long-lived.

Like the 3-phenoxybenzyl esters, the new pyrethroids are capable of both geometrical and optical isomerism, the biological activity varying somewhat according to the specific isomer. The pure cis geometrical isomer of a substituted [1,1'-biphenyl]-3-ylmethyl 3-(2,2-dichloroethenyl)-2,2-dimethylcyclopropanecarboxylate is usually a more active insecticide and acaricide than the pure trans isomer, and the activity of a substituted [1,1'-biphenyl]-3-ylmethyl 3-(2,2-dichloroethenyl)-2,2-dimethylcyclopropanecarboxylate is a function of the cis/trans ratio.

Although the preparation and testing of racemic esters is described specifically below, the pure optical isomers also display biological activity in varying degrees. The term "substituted [1,1'-biphenyl]-3-ylmethyl 3-(2,2-dihaloethenyl)-2,2-dimethylcyclopropanecarboxylate" employed herein is intended to include generically all optical and geometrical isomers of the named compounds and mixtures thereof. The term "lower" modifying alkyl or alkoxy means a linear or branched chain of 1–6, preferably 1–4, carbon atoms. The term "halo" employed alone or modifying alkyl means fluorine, chlorine or bromine.

Substituted [1,1'-biphenyl]-3-ylmethyl 3-(2,2-dihaloethenyl)-2,2-dimethylcyclopropanecarboxylates of this invention are represented by the formula

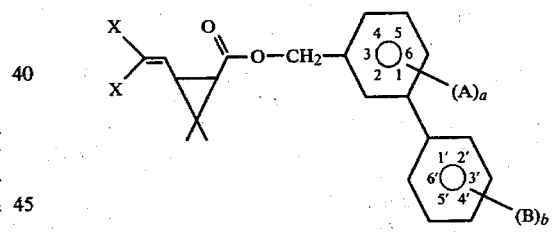

wherein X is chloro or bromo, and
b is 0, a is 1–4, and
when a is 1,
A is 2-, 4-, or 6-halo, 5-fluoro, 2-lower alkyl, 2-trifluoromethyl, and
when a is 2,
A is fluoro, 2 and 4-chloro, or 2 and 4-bromo, and
when a is 3 or 4,
A is fluoro;
or
a is 0, b is 1–5, and
when b is 1,
B is halo, 2' or 3'-lower alkyl, 2' or 3'-trifluoromethyl, or 2' or 3'-lower alkoxy, and
when b is 2,
B is fluoro, 2' and 4'-chloro, 2' and 4'-bromo, and
when b is 3, 4 or 5,
B is fluoro.

In general, it is preferred that X be chloro, since the dichloroethenyl compounds are less expensive to prepare. Of the lower alkyl and lower alkoxy substituents, methyl and ethyl and methoxy and ethoxy are preferred. Those compounds wherein a is 0 are desirable, especially those containing a single substituent, B, at the 2'-position. The most preferred compounds of this type are (2'-fluoro-[1,1'-biphenyl]-3-yl)methyl 3-(2,2-dichloroethenyl)-2,2-dimethylcyclopropanecarboxylate and (2'-methyl-[1,1'-biphenyl]-3-yl)methyl 3-(2,2-dichloroethenyl)-2,2-dimethylcyclopropanecarboxylate. When more than one substituent, B, is present, they are preferably halo, especially fluoro.

Among those compounds wherein b is 0, (2-methyl-[1,1'-biphenyl]-3-yl)methyl 3-(2,2-dichloroethenyl)-2,2-dimethylcyclopropanecarboxylate is very active, and among the halo-substituted compounds it is preferred that A be fluoro or chloro, especially fluoro. When the compound has 2-halo substitution, it is preferred that it also be substituted at the 4-position. Among these latter compounds, the cis-isomers are especially active, and so preferred. Most preferred of the cis-isomers are (2,4-dichloro-[1,1'-biphenyl]-3-yl)methyl cis-3-(2,2-dichloroethenyl)-2,2-dimethylcyclopropanecarboxylate and (2,4-difluoro-[1,1'-biphenyl]-3-yl)methyl cis-3-(2,2-dichloroethenyl)-2,2-dimethylcyclopropanecarboxylate.

Also within the contemplation of this invention are insecticidal and acaricidal compositions comprising an insecticidally or acaricidally effective amount of substituted [1,1'-biphenyl]-3-ylmethyl 3-(2,2-dihaloethenyl)-2,2-dimethylcyclopropanecarboxylate in admixture with an agriculturally acceptable carrier and a method of controlling insects or acarids which comprises applying to the locus where control is desired an insecticidally or acaricidally effective amount of substituted [1,1'-biphenyl]-3-ylmethyl 3-(2,2-dihaloethenyl)-2,2-dimethylcyclopropanecarboxylate.

The substituted [1,1'-biphenyl]-3-ylmethyl 3-(2,2-dihaloethenyl)-2,2-dimethylcyclopropanecarboxylates of this invention are prepared either by the reaction between a 3-(2,2-dihaloethenyl)-2,2-dimethylcyclopropanecarbonyl chloride and an appropriately substituted [1,1'-biphenyl]-3-ylmethyl alcohol or by reacting a sodium or potassium 3-(2,2-dihaloethenyl)-2,2-dimethylcyclopropanecarboxylate with a substituted [1,1'-biphenyl]-3-ylmethyl bromide, as disclosed in copending U.S. Patent Application Ser. No. 844,099, filed Oct. 20, 1977, now U.S. Pat. No. 4,130,657, which disclosure is incorporated herein by reference. These syntheses, illustrated in Examples 1 and 2 below, are processes of this invention.

3-(2,2-Dichloroethenyl)- and 3-(2,2-dibromoethenyl)-2,2-dimethylcyclopropanecarboxylic acid and corresponding carbonyl chlorides are obtained by methods disclosed in U.S. Pat. No. 4,024,163 and in Coll. Czech. Chem. Comm., 24, 2230 (1959). These disclosures are also incorporated herein by reference.

The pure cis or trans cyclopropanecarboxylates are prepared either by reacting pure cis or pure trans cyclopropanecarboxylic acid derivatives with appropriate substituted [1,1'-biphenyl]-3-ylmethyl compounds or by separating cis,trans mixtures using chromatographic techniques. The identities of the cis and trans isomers are established by reference to their nmr spectra, especially the patterns at 5.44–5.71 ppm and 6.10–6.40 ppm for the trans and cis isomers, respectively.

The substituted [1,1'-biphenyl]-3-ylmethyl compounds, which are intermediate in the preparation of the insecticidal esters, are novel compositions of matter and are also within the scope of this invention. These intermediates are described by the formula

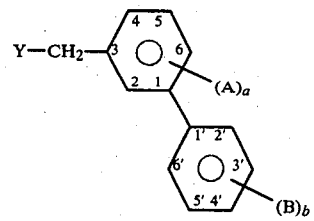

wherein Y is hydroxyl or bromo, and
b is 0, a is 1–4, and
when a is 1,
A is 2-, 4- or 6-halo, 5-fluoro, 2-lower alkyl, 2-trifluoromethyl, and
when a is 2,
A is fluoro, 2 and 4-chloro, or 2 and 4-bromo, and
when a is 3 or 4,
A is fluoro;
or
a is 0, b is 1–5, and
when b is 1,
B is halo, 2' or 3'-lower alkyl, 2' or 3'-trifluoromethyl, or 2' or 3'-lower alkoxy, and
when b is 2,
B is fluoro, 2' and 4'-chloro, 2' and 4'-bromo, and
when b is 3, 4 or 5,
B is fluoro.

Methyl, ethyl, and methoxy, ethoxy are preferred lower alkyl and lower alkoxy substituents respectively.

Those compounds wherein a is 0 are desirable, especially those containing a single substituent, B, at the 2'-position, most especially fluoro or methyl. When more than one substituent, B, is present, they are preferably halo, especially fluoro. Among those compounds wherein b is 0, it is preferred that A be fluoro or chloro, especially fluoro. When the compound has 2- substitution, it is preferred that it also be substituted at the 4-position when A is halo. 2-Methyl[1,1'-biphenyl]-3-ylmethyl compounds are attractive.

The substituted [1,1'-biphenyl]-3-ylmethyl alcohol and bromide intermediates are obtained by one or more of several different methods, depending on the specific compounds desired. These methods A-G, are described below. In addition, a substituted [1,1'-biphenyl]-3-ylmethyl alcohol, prepared by one of these methods, can be converted into the corresponding substituted [1,1'-biphenyl]-3-ylmethyl bromide by treating a solution of the alcohol in ether with phosphorous tribromide or phosphorous pentabromide. Similarly, a substituted [1,1-biphenyl]-3-ylmethyl bromide can be converted into the corresponding alcohol by first treating the bromide with sodium acetate in acetic acid, and then treating the thus produced biphenyl acetate with sodium hydroxide in methanol. These techniques are available in the prior art.

Table 1 lists specific examples of substituted [1,1'-biphenyl]-3-ylmethyl 3-(2,2-dihaloethenyl)-2,2-dimethylcyclopropanecarboxylates within the scope of this invention. Table 2 tabulates the physical properties of the exemplary insecticidal esters of Table 1, methods to prepare the substituted [1,1'-biphenyl]-3-ylmethyl alcohols or bromides employed in making the esters, and physical properties of the intermediate alcohols or bromides.

Unless otherwise indicated, all temperatures are in degrees Celsius and pressures are in millimeters of mercury. Proton chemical shifts, taken from nmr spectra in CDCl$_3$, are reported in ppm with respect to tetramethylsilane.

Method A

3-Bromomethyl[1,1'-biphenyl] compounds with (A) substituents are prepared by modification of a diazotization reaction. Thus, the appropriately substituted metatoluidine is converted to an acetamide, and this is treated with nitrosyl sulfuric acid to give the corresponding nitrosoacetamide, which is subsequently decomposed in benzene to the substituted 3-methylbiphenyl. Treatment with N-bromosuccinimide gives the 3-bromomethyl compound.

For example, to a stirred solution of 2,4-difluoro-3-methylaniline (24.3 g, 0.17 mole) in pyridine (14.1 ml, 0.19 mole) was slowly added acetyl chloride (13.3 ml, 0.19 mole). Upon complete addition, the reaction mixture was stirred at room temperature for 3 hours, then heated for one hour. The reaction mixture was extracted four times with diethyl ether. The combined extracts were washed three times with water, twice with aqueous 2% hydrochloric acid, water, then aqueous 5% sodium bicarbonate, water, and aqueous saturated sodium chloride solution, in that order. The organic layer was dried over magnesium sulfate and filtered. The filtrate was evaporated under reduced pressure, leaving as a solid residue 2,4-difluoro-3-methylacetanilide (27.4 g).

To a stirred solution of 2,4-difluoro-3-methylacetanilide (13.7 g, 0.074 mole) in 300 ml of benzene was added sodium acetate (12.1 g, 0.148 mole). The mixture was cooled to 5°, and nitrosyl hydrogen sulfate (9.4 g, 0.074 mole) was added in one portion. The reaction mixture was stirred for 2 hours at 0°. The reaction mixture was then allowed to warm to room temperature and then heated under reflux for 1.5 hours. The reaction mixture was cooled and washed twice with water, twice with aqueous 10% sodium carbonate, twice with water, twice with aqueous 5% sodium bicarbonate, twice with water, and then with aqueous saturated sodium chloride solution. The organic layer was separated, dried over magnesium sulfate and filtered. The filtrate was evaporated under reduced pressure to a solid residue. The residue was purified by column chromatography on silica gel to give 2,4-difluoro-3-methyl[1,1'-biphenyl] (2.2 g) as an oil.

A stirred solution of 2,4-difluoro-3-methyl[1,1'-biphenyl] (2.2 g, 0.011 mole) and N-bromosuccinimide (1.9 g, 0.011 mole) in 100 ml of carbon tetrachloride was irradiated with a 250 watt infrared lamp for 4 hours. The reaction mixture was allowed to reflux from the heat of the lamp. The reaction mixture was then filtered, and the filter cake was washed with three portions of carbon tetrachloride. The washes and filtrate were combined and evaporated under reduced pressure to give 3-bromomethyl-2,4-difluoro[1,1'-biphenyl] (3.5 g) as an oil whose nmr spectrum was consistent with that expected for the named compound.

In addition to those substituted [1,1'-biphenyl]-3-ylmethyl compounds listed in Table 2 as capable of preparation by this method, 3-bromomethyl-5-fluoro, 3-bromomethyl-6-bromo, and 3-bromomethyl-2,4-dibromo-[1,1'-biphenyl] are also prepared by method A.

EXAMPLE 1

(2,4-Difluoro-[1,1'-biphenyl]-3-yl)methyl 3-(2,2-dichloroethenyl)-2,2-dimethylcyclopropanecarboxylate To a mixture of cis-3-(2,2-dichloroethenyl)-2,2-dimethylcyclopropanecarboxylic acid (2.2 g, 0.11 mole) in 75 ml of heptane was added sodium hydroxide (0.42 g, 0.011 mole) in 5 ml of water. The mixture was shaken until the acid dissolved. The water was then removed by distillation, the volume of the reaction mixture being reduced to 50 ml. To the reaction mixture was added 3-bromomethyl-2,4-difluoro[1,1'-biphenyl] (3.0 g, 0.011 mole) and 0.1 gram of 1,4-diazabicyclo[2.2.2]octane in 35 ml of acetonitrile. The mixture was heated under reflux for 3 hours. The solvent was then removed by evaporation under reduced pressure, and the residue was partitioned between water and diethyl ether. The ether phase was washed with two portions of aqueous 2% hydrochloric acid, two portions of water, two portions of aqueous 10% sodium carbonate, two portions of water and one portion of aqueous saturated sodium chloride solution in that order. The washed ethereal solution was dried over magnesium sulfate, and the ether was evaporated under reduced pressure. The oily residue was purified by column chromatography on silical gel, elution with hexane. This afforded (2,4-difluoro-[1,1'-biphenyl]-3-yl)methyl cis-3-(2,2-dichloroethenyl)-2,2-dimethylcyclopropanecarboxylate (1.8 g), Example XIV in Table 1.

Method B

3-Bromomethyl[1,1'-biphenyl] compounds, especially those with B substituents, are in general prepared by an extension of the Knoevenagel condensation of ethyl acetoacetate with substituted benzaldehydes. The resultant α,β-unsaturated methyl ketone is reduced with sodium borohydride to the alcohol, which is simultaneously dehydrated and dehydrogenated with either sulfur or palladium on charcoal, followed by treatment with N-bromosuccinimide.

For example, with stirring, 2-fluorobenzaldehyde (30.0 g, 0.24 mole), ethyl acetoacetate (63.0 g, 0.48 mole), 1 ml of diethylamine, and 15 ml of ethanol were combined. The exotherm was controlled by cooling the mixture for approximately 2 minutes in an ice bath. The reaction mixture was then stirred at room temperature for 5 days. Each day an additional 1 ml of an ethanolic solution containing 20% diethylamine was added. After 5 days, the solvent was removed from the reaction mixture by evaporation under reduced pressure to give ethyl α,α-diacetyl-β-2-fluorophenylglutarate.

The ethyl α,α-diacetyl-β-2-fluorophenylglutarate was heated under vacuum at 160°–180°/10–15 mm for 1 hr, eliminating carbon dioxide and ethanol and producing 5-(2-fluorophenyl)-3-methyl- To 5-(2-fluorophenyl)-3-methyl-4-carbethoxy-2-cyclohexen-1-one (57.3 g, 0.21 mole) was added a solution of sodium hydroxide (11.5 g, 0.29 mole) in 35 ml of ethanol and 80 ml of water. The stirred reaction mixture was heated under reflux for 8 hours. The ethanol was removed by evaporation under reduced pressure, and the residue was extracted with diethyl ether. The ether extract was dried over sodium sulfate and filtered. The filtrate was evaporated under reduced pressure to give 5-(2-fluorophenyl)-3-methyl-2-cyclohexen-1-one (42.3 g).

To a stirred mixture of sodium borohydride (2.0 g, 0.05 mole) in 400 ml of ethanol was added in one portion 5-(2-fluorophenyl)-3-methyl-2-cyclohexen-1-one (42.3 g, 0.21 mole) in 50 ml of ethanol. The reaction mixture was heated under reflux for 16 hours. An additional 2.0 g of sodium borohydride was then added to the reaction mixture and heating under reflux continued for an additional 2 hours. Again, 2.0 g of sodium borohydride was added to the reaction mixture and heating under reflux continued for a 2 hour period. The reaction mixture was stirred with ice, then acidified with aqueous 10% hydrochloric acid. The mixture was extracted with diethyl ether, and the ether extract was washed with an aqueous solution saturated with sodium bicarbonate. The organic layer was dried with sodium sulfate and filtered. The filtrate was evaporated under reduced pressure to give 5-(2-fluorophenyl)-3-methyl-2-cyclohexen-1-ol (41.2 g) as an oil.

A mixture of 5-(2-fluorophenyl)-3-methyl-2-cyclohexen-1-ol (16.6 g, 0.08 mole) and sulfur (7.8 g, 0.24 mole) was heated at 180°–230° for 7.5 hours. The reaction mixture then stood at room temperature for approximately 60 hours before it was distilled under reduced pressure to give 2'-fluoro-3-methyl[1,1'-biphenyl].

A mixture of 2'-fluoro-3-methyl[1,1'-biphenyl] (1.1 g, 0.006 mole) and N-bromosuccinimide (1.1 g, 0.006 mole) in 11 ml of carbon tetrachloride was irradiated with white light to afford 3-bromomethyl-2'-fluoro[1,1'-biphenyl] (1.3 g). The nmr spectrum was consistent with that expected for the named compound.

In addition to those substituted [1,1'-biphenyl]-3-ylmethyl compounds listed in Table 2 as capable of preparation by this method, 3-bromomethyl-2-halo, 3-bromomethyl-2-trifluoromethyl, 3-bromomethyl-2'-bromo, 3-bromomethyl-3'-bromo, 3-bromomethyl-4'-bromo, 3-bromomethyl-2'-trifluoromethyl, 3-bromomethyl-3'-lower alkoxy and 3-bromomethyl-2',4'-dibromo[1,1'-biphenyl] are also prepared by method B.

Method C

Alternately, B ring substituted 3-bromomethyl[1,1'-biphenyl] compounds are prepared by the reaction of an appropriately substituted phenyl magnesium bromide with a 3-methylcyclohexanone, followed by dehydration and dehydrogenation with sulfur or palladium on charcoal, to give a substituted 3-methyl[1,1'-biphenyl], which is then treated with N-bromosuccinimide.

For example, magnesium turnings (6.4 g, 0.26 mole) were flame-dried, the containing glassware was cooled, and 3-bromochlorobenzene (50 g, 0.26 mole), in 50 ml of diethyl ether was added. As the reaction began, an additional 200 ml of diethyl ether was added, and the reaction mixture was heated under reflux for 0.5 hour. To the refluxing reaction mixture was added dropwise, during a 0.5 hour period, 3-methylcyclohexanone (29.2 g, 0.26 mole) in 100 ml of diethyl ether. Upon complete addition, the reaction mixture was heated under reflux for an additional 0.5 hour, then poured into 500 ml of icewater containing 50 ml of hydrochloric acid. The mixture was extracted with three 200 ml portions of diethyl ether. The combined extract was washed twice with 100 ml portions of an aqueous solution saturated with sodium chloride. After separation, the organic layer was dried over sodium sulfate and filtered. The filtrate was evaporated under reduced pressure to an oil. The oil was purified by distillation using a Kugelrohr distilling system at 85°/0.05 mm for 2.5 hours to give 1-(3-chlorophenyl)-3-methylcyclohexan-1-ol (25 g).

A mixture of 1-(3-chlorophenyl)-3-methylcyclohexan-1-ol (25.0 g, 0.11 mole) and sulfur (7.1 g, 0.22 mole) was heated at 250° for 4.5 hours. The reaction mixture then stood at room temperature for approximately 60 hours, and then it was distilled under reduced pressure to give 19.5 grams of distillate; bp, 150°–165°/10 mm. The distillate was chromatographed on silica gel, elution with hexane. The eluent was evaporated under reduced pressure to give 3'-chloro-3-methyl[1,1'-biphenyl] (17.0 g) as an oil. The nmr and the ir spectra of the oil were consistent with the proposed structure.

3'-Chloro-3-methyl[1,1'-biphenyl] (7.0 g, 0.035 mole) and N-bromosuccinimide (6.4 g, 0.035 mole) in 100 ml of carbon tetrachloride were irradiated for 4 hours with white light to afford 3-bromomethyl-3'-chloro[1,1'-biphenyl] (9.2 g). The nmr spectrum was consistent with that expected for the named compound.

Method D 3-(2,3,4,5,6-Pentafluorophenyl)benzyl alcohol was prepared as follows: Under an argon atmosphere, methyl 3-iodobenzoate (2.3 g. 0.009 mole) and 2,3,4,5,6-pentafluorophenyl copper (2.0 g, 0.009 mole) were added to 50 ml of toluene. The stirred reaction mixture was heated under reflux for 2 hours, then cooled to room temperature. The mixture was filtered and the filtrate evaporated under reduced pressure to a residual solid. The solid was recrystallized from methanol to give methyl 3-(2,3,4,5,6-pentafluorophenyl)benzoate (2.6 g); mp, 104°–106°.

To a stirred suspension of 0.5 g of lithium aluminum hydride in 50 ml of dry tetrahydrofuran, cooled to −78°, was added dropwise methyl 3-(2,3,4,5,6-pentafluorophenyl)benzoate (2.6 g, 0.009 mole) in 50 ml of dry tetrahydrofuran. Upon complete addition, the reaction mixture was stirred while warming to room temperature. A solution of 10% water in tetrahydrofuran was then added dropwise to the reaction mixture to destroy excess lithium aluminum hydride. An additional 50 ml of water was then added, and the liquid phases separated. The aqueous layer was washed with two 50 ml portions of diethyl ether. The ether washes were combined with the organic layer from the reaction mixture and dried. The mixture was filtered and the filtrate evaporated under reduced pressure to give 3-(2,3,4,5,6-pentafluorophenyl)benzyl alcohol (3.0 g) as an oil, which solidified on standing. The ir spectrum was consistent with the proposed structure.

Method E

3-Bromomethyl-3'-methyl[1,1'-biphenyl] was prepared by treating 3,3'-dimethyl[1,1'-biphenyl] (20.0 g, 0.11 mole) with N-bromosuccinimide (18.9 g, 0.11 mole) in the presence of 0.1 g of benzoyl peroxide in 130 ml of carbon tetrachloride. Irradiation of the reaction mixture with white light afforded 3-bromomethyl-3'-methyl[1,1'-biphenyl] (4.5 g). The nmr and the ir spectra were consistent with the proposed structure.

Method F 3-(2-Methylphenyl)benzyl alcohol was prepared as follows: Under a nitrogen atmosphere a stirred mixture of magnesium turnings (3.0 g, 0.12 mole) and 10 ml of 1,2-dibromoethane in 100 ml of dry tetrahydrofuran was heated to 30°. To the stirred mixture was added dropwise 4,5-dihydro-4,4-dimethyl-2-(3-bromophenyl)oxazole (26.9 g, 0.11 mole) in 50 ml of dry tetrahydrofuran. Upon complete addition, the reaction mixture was heated at reflux for 1.5 hours. The so-prepared Grignard reagent was cooled, placed in a dropping funnel, and added dropwise at 0° to a stirred solution of 2-bromotoluene (18.1 g, 0.11 mole) and 0.5 g of bis(1,3-diphenylphosphino)propanenickel(II) chromate in 150 ml of dry tetrahydrofuran. The temperature of the reaction mixture was maintained at 0° throughout the addition. Upon complete addition, the temperature was allowed to rise to 15°, and the reaction mixture was stirred for 16 hours, then heated under reflux for approximately 24 hours. The reaction mixture was cooled and poured into 500 ml of water. The resultant emulsion was broken by pouring small amounts of the mixture into 1000 ml portions of water. Each portion was extracted with two 200 ml portions of toluene. The combined toluene extracts were evaporated under reduced pressure to afford 25 g of oily residue. The combined water layers were divided into three parts, and to each part was added 10 ml of 6 N hydrochloric acid. Each part was extracted with toluene. The combined extracts were evaporated under reduced pressure to give an additional 8.8 g of oily residue. The residues were combined and impurities removed by distillation using a Kugelrohr distilling system. The residue was purified by column chromatography on silica gel, producing 4,5-dihydro-4,4-dimethyl-2-[(2'-methyl[1,1'biphenyl]-3-yl)oxazole (7.2 g).

A stirred solution of 10.5 g 4,5-dihydro-4,4-dimethyl-2-(2'-methyl[1,1'-biphenyl]-3-yl)oxazole and 17.8 ml of concentrated sulfuric acid in 250 ml of ethanol was heated at reflux for 16 hours. The reaction mixture was cooled to room temperature and poured into 150 ml of water. The mixture was treated with 250 ml of aqueous 5% sodium bicarbonate and extracted four times with 250 ml portions of diethyl ether. The combined ether extracts were dried over magnesium sulfate and filtered. The filtrate was evaporated under reduced pressure to a residue. The residue was taken up in 150 ml of methylene chloride and filtered. The filtrate was evaporated under reduced pressure, and the solid residue was purified by column chromatography on silica gel to produce ethyl (2'methyl[1,1'-biphenyl]-3-carboxylate (4.7 g).

To a stirred suspension of 0.6 g of lithium aluminum hydride in 50 ml of dry tetrahydrofuran was added dropwise, during a 20 minute period, 4.7 g of ethyl (2'methyl-[1,1'-biphenyl])-3-carboxylate in 10 ml of tetrahydrofuran. Upon complete addition, the reaction mixture was heated under reflux for 1.5 hour, then cooled to room temperature. Excess lithium aluminum hydride was destroyed by the addition of a few drops of ethyl acetate. The reaction mixture was poured into water and the mixture extracted with ether. The extract was dried over magnesium sulfate and filtered. The filtrate was evaporated under reduced pressure to any oily residue of 3(2-methylphenyl)benzyl alcohol (3.1 g). The ir spectrum of the product was consistent with that expected.

Example 2

(2'-Methyl-[1,1'-biphenyl]-3-yl)methyl 3-(2,2-dichloroethenyl)-2,2-dimethylcyclopropanecarboxylate To a stirred solution of 3-(2-methylphenyl)benzyl alcohol (3.1 g, 0.016 mole) and 2 ml of pyridine in 65 ml of dry toluene was added dropwise (3.6, 0.010 mole) cis, trans-3-(2,2-dichloroethenyl)-2,2-dimethylcyclopropanecarbonyl chloride. The reaction mixture was then stirred at room temperature for 16 hours, and then poured into 100 ml of water and shaken. The toluene layer was separated and washed successively with 50 ml of dilute hydrochloric acid, 50 ml of dilute sodium hydroxide solution, and two 300 ml portions of water. The washed toluene layer was dried over magnesium sulfate, and the toluene was removed by evaporation under reduced pressure. The residue was purified by column chromatography on silica gel, elution with 1:1 chloroform: hexane to afford (2'-methyl-[1,1'-biphenyl]-3-yl)methyl cis, trans-3-(2,2-dichloroethenyl)2,2-dimethylcyclopropanecarboxylate (4.9 g), Example XIX in Table 1.

Method G

2-Methyl[1,1'-biphenyl]-3-methanol was prepared as follows: To 100 ml of stirred 50% aqueous ethanol was added 2-methyl-3-nitrobenzyl alcohol (41.8 g, 0.25 mole) and 85.0 grams of iron powder. The mixture was brought to reflux, and 5.2 ml of concentrated hydrochloric acid was slowly added. Upon complete addition, the reaction mixture was stirred under reflux for 2 hours. The reaction mixture was then made just basic with ethanolic 15% potassium hydroxide. The hot mixture was filtered through diatomaceous earth to remove the iron. The filter cake was washed with ethanol. The filtrate was acidified with hydrogen chloride, then allowed to stand at room temperature for 16 hours. The ethanol was removed by evaporation under reduced pressure. Hexane was added to the residue, and the water-hexane azeotrope was removed by distillation. The addition of hexane and the subsequent removal of the water-hexane azeotrope by distillation was repeated three times. The 3-hydroxymethyl-2-methylaniline hydrochloride residue thus obtained was used as follows.

A stirred solution of 3-hydroxymethyl-2-methylaniline hydrochloride (43.4 g, 0.25 mole) and 17.2 ml of concentrated sulfuric acid in ice-water was cooled to 0°, and a solution of sodium nitrite (17.3 g, 0.25 mole) in water was added dropwise. Upon complete addition, the reaction mixture was stirred for an additional 0.5 hour, then an additional 8 ml of concentrated sulfuric acid was added dropwise. With the temperature maintained at 0°, a solution of potassium iodide (49.8 g, 0.30 mole) in water was added dropwise to the reaction mixture, followed by the addition of 0.1 gram of copper powder. The reaction mixture was slowly warmed to 70° where it stirred for 1 hour. The reaction mixture was then allowed to stand for 18 hours while cooling to room temperature. The reaction mixture was then taken up in water and extracted with chloroform. The chloroform extract was washed with an aqueous saturated solution of sodium bisulfite, then with water. The chloroform layer was dried and filtered. The filtrate was evaporated under reduced pressure to give 3iodo-2-methylbenzyl alcohol (15.2 g) as a dark solid.

In a photoreactor was placed 3-iodo-2-methylbenzyl alcohol (5.0 g, 0.02 mole) and 800 ml of benzene. To this was added sodium thiosulfate (5.0 g, 0.04 mole) in 15 ml of water. The mixture was purged with argon for 30 minutes, then irradiated with a 200 watt medium pressure ultraviolet lamp for 36.5 hours. The reaction mixture was then transferred to a separatory funnel. The photoreactor was washed with approximately 20 ml each of water, chloroform, and acetone. These washes were added to the separatory funnel. The organic layer was washed with aqueous 0.5 M sodium thiosulfate, then with an aqueous solution saturated with sodium chloride. The organic layer was then dried and filtered.

The filtrate was evaporated under reduced pressure to an oily residue. The residue was purified by column chromatography on silica gel, elution with 1:1 hexane:chloroform, to give 2-methyl[1,1'-biphenyl]-3-methanol (2.4 g). The nmr and ir spectra were consistent with that expected for the named compound.

Table 1

| Ex. | Name of Ester |
|---|---|
| I | (4-Fluoro-[1,1'-biphenyl]-3-yl)methyl cis,trans-3-(2,2-dichloroethenyl)-2,2-dimethylcyclopropanecarboxylate |
| II | (6-Fluoro-[1,1'-biphenyl]-3-yl)methyl cis-3-(2,2-dichloroethenyl)-2,2-dimethylcyclopropanecarboxylate |
| III | (6-Fluoro-[1,1'-biphenyl]-3-yl)methyl trans-3-(2,2-dichloroethenyl)-2,2-dimethylcyclopropanecarboxylate |
| IV | (4-Chloro-[1,1'-biphenyl]-3-yl)methyl cis,trans-3-(2,2-dichloroethenyl)-2,2-dimethylcyclopropanecarboxylate |
| V | (6-Chloro-[1,1'-biphenyl]-3-yl)methyl cis,trans-3-(2,2-dichloroethenyl)-2,2-dimethylcyclopropanecarboxylate |
| VI | (6-Chloro-[1,1'-biphenyl]-3-yl)methyl cis-3-(2,2-dichloroethenyl)-2,2-dimethylcyclopropanecarboxylate |
| VII | (6-Chloro-[1,1'-biphenyl]-3-yl)methyl trans-3-(2,2-dichloroethenyl)-2,2-dimethylcyclopropanecarboxylate |
| VIII | (4-Bromo-[1,1'-biphenyl]-3-yl)methyl cis,trans-3-(2,2-dichloroethenyl)-2,2-dimethylcyclopropanecarboxylate |
| IX | (4-Bromo-[1,1'-biphenyl]-3-yl)methyl cis-3-(2,2-dichloroethenyl)-2,2-dimethylcyclopropanecarboxylate |
| X | (4-Bromo-[1,1'-biphenyl]-3-yl)methyl trans-3-(2,2-dichloroethenyl)-2,2-dimethylcyclopropanecarboxylate |
| XI | (2,4-Dichloro-[1,1'-biphenyl]-3-yl)methyl cis,trans-3-(2,2-dichloroethenyl)-2,2-dimethylcyclopropanecarboxylate |
| XII | (2,4-Dichloro-[1,1'-biphenyl]-3-yl)methyl cis-3-(2,2-dichloroethenyl)-2,2-dimethylcyclopropanecarboxylate |
| XIII | (2,4-Dichloro-[1,1'-biphenyl]-3-yl)methyl trans-3-(2,2-dichloroethenyl)-2,2-dimethylcyclopropanecarboxylate |
| XIV | (2,4-Difluoro-[1,1'-biphenyl]-3-yl)methyl cis-3-(2,2-dichloroethenyl)-2,2-dimethylcyclopropanecarboxylate |
| XV | (3'-Methyl-[1,1'-biphenyl]-3-yl)methyl cis,trans-3-(2,2-dichloroethenyl)-2,2-dimethylcyclopropanecarboxylate |
| XVI | (2',3',4',5',6'-Pentafluoro-[1,1'-biphenyl]-3-yl)methyl cis,trans-3-(2,2-dichloroethenyl)-2,2-dimethylcyclopropanecarboxylate |
| XVII | (2',3',4',5',6'-Pentafluoro-[1,1'-biphenyl]-3-yl)methyl cis-3-(2,2-dichloroethenyl)-2,2-dimethylcyclopropanecarboxylate |
| XVIII | (2',3',4',5',6'-Pentafluoro-[1,1'-biphenyl]-3-yl)methyl trans-3-(2,2-dichloroethenyl)-2,2-dimethylcyclopropanecarboxylate |
| XIX | (2'-Methyl-[1,1'-biphenyl]-3-yl)methyl cis,trans-3-(2,2-dichloroethenyl)-2,2-dimethylcyclopropanecarboxylate |
| XX | (3'-Chloro-[1,1'-biphenyl]-3-yl)methyl cis,trans-3-(2,2-dichloroethenyl)-2,2-dimethylcyclopropanecarboxylate |
| XXI | (3'-Chloro-[1,1'-biphenyl]-3-yl)methyl cis-3-(2,2-dichloroethenyl)-2,2-dimethylcyclopropanecarboxylate |
| XXII | (3'-Chloro-[1,1'-biphenyl]-3-yl)methyl trans-3-(2,2-dichloroethenyl)-2,2-dimethylcyclopropanecarboxylate |
| XXIII | (2'-Fluoro-[1,1'-biphenyl]-3-yl)methyl cis,trans-3-(2,2-dichloroethenyl)-2,2-dimethylcyclopropanecarboxylate |
| XXIV | (3'-Fluoro-[1,1'-biphenyl]-3-yl)methyl cis,trans-3-(2,2-dichloroethenyl)-2,2-dimethylcyclopropanecarboxylate |
| XXV | (3'-Fluoro-[1,1'-biphenyl]-3-yl)methyl cis-3-(2,2-dichloroethenyl)-2,2-dimethylcyclopropanecarboxylate |
| XXVI | (3'-Fluoro-[1,1'-biphenyl]-3-yl)methyl trans-3-(2,2-dichloroethenyl)-2,2-dimethylcyclopropanecarboxylate |
| XXVII | (4'-Fluoro-[1,1'-biphenyl]-3-yl)methyl cis,trans-3-(2,2-dichloroethenyl)-2,2-dimethylcyclopropanecarboxylate |
| XXVIII | (4'-Fluoro-[1,1'-biphenyl]-3-yl)methyl cis-3(2,2-dichloroethenyl)-2,2-dimehtylcyclopropanecarboxylate |
| XXIX | (4'-Fluoro-[1,1'-biphenyl]-3-yl)methyl trans-3-(2,2-dichloroethenyl)-2,2-dimethylcyclopropanecarboxylate |
| XXX | (2'-Chloro-[1,1'-biphenyl]-3-yl)methyl cis,trans-3-(2,2-dichloroethenyl)-2,2-dimethylcyclopropanecarboxylate |
| XXXI | (2'-Chloro-[1,1'-biphenyl]-3-yl)methyl cis-3-(2,2-dichloroethenyl)-2,2-dimethylcyclopropanecarboxylate |
| XXXII | (2'-Chloro-[1,1'-biphenyl]-3-yl)methyl trans-3-(2,2-dichloroethenyl)-2,2-dimethylcyclopropanecarboxylate |
| XXXIII | (3'-Trifluoromethyl-[1,1'-biphenyl]-3-yl)methyl cis,trans-3-(2,2-dichloroethenyl)-2,2-dimethylcyclopropanecarboxylate |
| XXXIV | (2'-Methoxy-[1,1'-biphenyl]-3-yl)methyl cis,trans-3-(2,2-dichloroethenyl)-2,2-dimethylcyclopropanecarboxylate |
| XXXV | (2'-Methoxy-[1,1'-biphenyl]-3-yl)methyl cis-3-(2,2-dichloroethenyl)-2,2-dimethylcyclopropanecarboxylate |
| XXXVI | (2',4'-dichloro-[1,1'-biphenyl]-3-yl)methyl cis,trans-3-(2,2-dichloroethenyl)-2,2-dimethylcyclopropanecarboxylate |
| XXXVII | (2-Methyl[1,1'-biphenyl]-3-yl)methyl cis-3-(2,2-dichloroethenyl)-2,2-dimethylcyclopropanecarboxylate |

Table 2

| | Intermediate Alcohol or Bromide | | Ester Identifying Properties | | | | | |
|---|---|---|---|---|---|---|---|---|
| | | nmr Spectrum, 3- | | | Elemental Analysis | | | |
| | Methyl | methyl protons only | | | Calc. | | Found | |
| Ex. | Of Prep | all (s,3H) | % cis | % trans | C | H | C | H |
| I | A | 4.60 | 32 | 68 | 64.13 | 4.87 | 64.23 | 4.87 |
| II | A | 4.60 | 100 | | 64.13 | 4.87 | 64.37 | 5.02 |
| III | A | | | 100 | 64.13 | 4.87 | 64.14 | 4.99 |
| IV | A | 4.82 | 37 | 63 | 61.56 | 4.67 | 61.33 | 4.65 |
| V | A | 4.43 | 44 | 56 | 61.56 | 4.67 | 61.68 | 4.76 |
| VI | A | | 100 | | 61.56 | 4.67 | 61.64 | 4.64 |
| VII | A | | | 100 | | | | |
| VIII | A | 4.63 | 53 | 47 | 55.54 | 4.21 | 55.67 | 4.06 |
| IX | A | | 100 | | 55.54 | 4.21 | 55.45 | 4.23 |
| X | A | | | 100 | | | | |
| XI | A | 4.83 | 44 | 56 | 56.79 | 4.08 | 56.74 | 4.17 |
| XII | A | | 100 | | | | | |
| XIII | A | | | 100 | | | | |

Table 2-continued

| Ex. | | | | | | | | | |
|---|---|---|---|---|---|---|---|---|---|
| XIV | A | | 4.56 | 100 | | 61.38 | 4.41 | 61.01 | 4.37 |
| XV | E | | 4.48 | 60 | 40 | 67.85 | 5.71 | 67.21 | 5.96 |
| XVI | D | | | 40 | 60 | 54.21 | 3.25 | 54.81 | 3.47 |
| XVII | D | | | 100 | | 54.21 | 3.25 | 54.80 | 3.64 |
| XVIII | D | | | | 100 | 54.21 | 3.25 | 55.11 | 3.52 |
| XIX | F | | | 33 | 67 | 67.86 | 5.71 | 67.64 | 5.72 |
| XX | C | | 4.47 | 50 | 50 | 61.56 | 4.67 | 60.70 | 4.56 |
| XXI | C | | | 100 | | 61.56 | 4.67 | 61.43 | 4.91 |
| XXII | C | | | | 100 | | | | |
| XXIII | B | | 4.50 | 50 | 50 | 64.13 | 4.80 | 64.42 | 4.69 |
| XXIV | C | | 4.48 | 46 | 54 | 64.13 | 4.87 | 63.99 | 4.63 |
| XXV | C | | | 100 | | | | | |
| XXVI | C | | | | 100 | | | | |
| XXVII | C | | | 27 | 73 | | | | |
| XXVIII | C | | | | 100 | 64.13 | 4.80 | 64.42 | 4.69 |
| XXIX | C | | | | | | | | |
| XXX | B | | 4.50 | 52 | 48 | 61.56 | 4.67 | 60.36 | 4.49 |
| XXXI | B | | | 100 | | 61.56 | 4.67 | 61.61 | 4.75 |
| XXXII | B | | | | 100 | | | | |
| XXXIII | B | | 4.57 | 48 | 52 | 59.61 | 4.32 | 59.21 | 4.19 |
| XXXIV | B | | 4.49 | 54 | 46 | 65.19 | 5.47 | 65.32 | 5.39 |
| XXXV | B | | | 100 | | | | | |
| XXXVI | B | | | 63 | 37 | 56.79 | 4.08 | 57.36 | 4.73 |
| XXXVII | G | | 4.70 | 100 | | | | | |

Ester Identifying Properties
nmr Spectrum

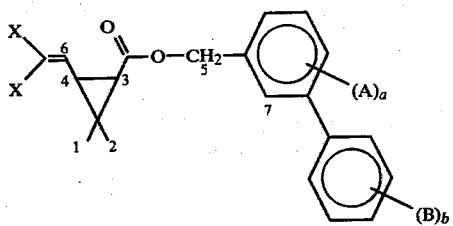

| Ex. | $H_1$ | $H_2$ | $H_3$ $H_4$ |
|---|---|---|---|
| I | 1.17(s,3H) 1.27(s,3H) | 1.23(s,3H) 1.30(s,3H) | 1.57–2.38(m,4H) |
| II | 1.22(s,3H) | 1.25(s,3H) | 1.77–2.17(m,2H) |
| III | 1.17(s,3H) | 1.27(s,3H) | 1.65–1.58(d,1H) 2.12–2.35(dd,1H) |
| IV | 1.15(s,3H) 1.25(s,3H) | 1.20(s,3H) 1.27(s,3H) | 1.63–2.39(m,4H) |
| V | 1.13(s,3H) 1.23(s,3H) | 1.20(s,3H) 1.27(s,3H) | 1.40–2.35(m,4H) |
| VI | 1.21(s,3H) | 1.27(s,3H) | 1.77–2.20(m,2H) |
| VII | 1.17(s,3H) | 1.27(s,3H) | 1.58–1.68 2.13–2.37 (d,1H) (dd,1H) |
| VIII | 1.17(s,3H) 1.25(s,3H) | 1.23(s,3H) 1.28(s,3H) | 1.63–2.40(m,4H) |
| IX | | | |
| X | 1.18(s,3H) | 1.30(s,3H) | 1.66–1.73(d,2H) 2.18–2.42(dd,2H) |
| XI | 1.15(s,3H) 1.25(s,3H) | 1.20(s,3H) 1.28(s,3H) | 1.58–2.37(m,4H) |
| XII | 1.20(s,3H) | 1.26(s,3H) | 1.77–2.18(m,2H) |
| XIII | 1.16(s,3H) | 1.30(s,3H) | 1.59–1.67 2.17–2.39 (d,1H) (dd,1H) |
| XIV | 1.18(s,3H) | 1.25(s,3H) | 1.72–2.14(m,2H) |
| XV | 1.13(s,3H) 1.26(s,3H) | 1.20(s,3H) 1.28(s,3H) | 1.57–2.36(m,4H) |
| XVI | 1.17(s,3H) 1.27(s,3H) | 1.24(s,6H) | 1.57–2.33(m,4H) |
| XVII | 1.23(s,6H) | | 1.78–2.18(m,2H) |
| XVIII | 1.17(s,3H) | 1.30(s,3H) | 1.57–1.67 2.10–2.33 (d,1H) (dd,1H) |
| XIX | 1.17(s,3H) 1.23(s,3H) | 1.20(s,3H) 1.25(s,3H) | 1,57–2.35(m,4H) |
| XX | 1.17(s,3H) 1.26(s,3H) | 1.23(s,3H) 1.30(s,3H) | 1.62–2.40(m,4H) |
| XXI | 1.23(s,3H) | 1.26(s,3H) | 1.80–2.20(m,2H) |
| XXII | 1.17(s,3H) | 1.32(s,3H) | 1.63–1.73 2.17–2.40 (d,1H) (dd,1H) |
| XXIII | 1.17(s,3H) 1.25(s,3H) | 1.23(bs,6H) | 1.58–2.23(m,4H) |
| XXIV | 1.13(s,3H) 1.23(s,3H) | 1.20(s,3H) 1.27(s,3H) | 1.57–2.34(m,4H) |
| XXV | | | |
| XXVI | 1.17(s,3H) | 1.30(s,3H) | 1.63–1.71(d,1H) |

Table 2-continued

| Ex. | | | |
|---|---|---|---|
| XXVII | 1.13(s,3H) | 1.20(s,3H) | 2.18–2.42(dd,1H) |
| | 1.23(s,3H) | 1.26(s,3H) | 1.57–2.33(m,4H) |
| XXVIII | | | |
| XXIX | 1.17(s,3H) | 1.32(s,3H) | 1.63–1.71(d,1H)  2.17–2.40(dd,1H) |
| XXX | 1.16(s,3H) | 1.22(s,3H) | 1.60–2.39(m,4H) |
| | 1.25(s,3H) | 1.28(s,3H) | |
| XXXI | 1.22(s,3H) | 1.23(s,3H) | 1.76–2.20(m,2H) |
| XXXII | 1.17(s,3H) | 1.30(s,3H) | 1.62–1.72(d,1H)  2.17–2.40(dd,1H) |
| XXXIII | 1.17(s,3H) | 1.23(s,3H) | 1.62–2.40(m,4H) |
| | 1.27(s,3H) | 1.30(s,3H) | |
| XXXIV | 1.13(s,3H) | 1.22(s,3H) | 1.58–2.33(m,4H) |
| XXXV | 1.18(s,3H) | 1,27(s,3H) | 1.68–2.16(m,2H) |
| XXXVI | 1.15(s,3H) | 1.25(s,3H) | 1.60–2.39)m,4H) |
| | 1.27(s,3H) | 1.30(s,3H) | |
| XXXVII | 1.24(s,3H) | 1.27(s,3H) | 1.68–2.21(m,2H) |

| Ex. | $H_5$ | $H_6$ | $H_7$ |
|---|---|---|---|
| I | 5.23(bs,4H) | 5.52–5.65(d,1H) | 6.95–7.65(m,16H) |
| | | 6.17–6.33(dd,1H) | |
| II | 5.08(s,2H) | 6.15–6.30(dd,1H) | 6.92–7.57(m,8H) |
| III | 5.10(s,2H) | 5.48–5.60(d,1H) | 6.91–7.53(m,8H) |
| IV | 5.26(s,2H) | 5.50–5.67(d,1H) | 7.17–7.62(m,16H) |
| | 5.28(s,2H) | 6.20–6.37(dd,1H) | |
| V | 5.10(s,2H) | 5.52–5.67(d,1H) | 7.13–7.51(m,16H) |
| | 5.13(s,2H) | 6.15–6.30(dd,1H) | |
| VI | 5.10(s,2H) | 6.17–6.33(dd,1H) | 7.13–7.52(m,8H) |
| VII | 5.13(s,2H) | 5.55–5.67(d,1H) | 7.03–7.42(m,8H) |
| VIII | 5.25(s,2H) | 5.55–5.68(d,1H) | 7.21–7.70(m,16H) |
| | 5.28(s,2H) | 6.20–6.35(dd,1H) | |
| IX | | | |
| X | 5.30(s,2H) | 5.57–5.70(d,1H) | 7.25–7.72(m,8H) |
| XI | 5.47(s,2H) | 5.57–5.67(d,1H) | 7.13–7.43(m,14H) |
| | 5.50(s,2H) | 6.20–6.37(dd,1H) | |
| XII | 5.50(s,2H) | 6.21–6.37(dd,1H) | 7.13–7.43(m,7H) |
| XIII | 5.52(s,2H) | 5.55–5.70(d,1H) | 7.13–7.50(m,7H) |
| XIV | 5.18–5.25(t,2H) | 6.17–6.28(dd,1H) | 6.74–7.55(m,7H) |
| XV | 5.09(s,2H) | 5.45–5.60(d,1H) | 2.36(s,6H) |
| | 5.13(s,2H) | 6.17–6.37(dd,1H) | 6.95–7.50(m,16H) |
| XVI | 5.13(s,4H) | 5.47–5.60(d,1H) | 6.78–7.46(m,8H) |
| | | 6.10–6.25(dd,1H) | |
| XVII | 5.17(s,2H) | 6.15–6.30(dd,1H) | 7.03–7.51(m,4H) |
| XVIII | 5.17(s,2H | 5.50–5.63(d,1H) | 6,83–7.48(m,4H) |
| XIX | 5.10(s,2H) | 5.48–5.61(d,1H) | 2.25(s,6H) |
| | 5.15(s,2H) | 6.15–6.30(dd,1H) | 7.07–7.51(m,16H) |
| XX | 5.17(s,2H) | 5.57–5.68(d,1H) | 7.23–7.63(m,16H) |
| | 5.21(s,2H) | 6.22–6.38(dd,1H) | |
| XXI | 5.18(s,2H) | 6.20–6.37(dd,1H) | 7.23–7.60(m,8H) |
| XXII | 5.22(s,2H) | 5.57–5.70(d,1H) | 7.25–7.70(m,8H) |
| XXIII | 5.13(bs,4H) | 5.48–5.63(d,1H) | 6.81–7.48(m,16H) |
| | | 6.13–6.30(dd,1H) | |
| XXIV | 5.10(s,2H) | 5.47–5.61(d,1H) | 6.77–7.45(m,8H) |
| | 5.13(s,2H) | 6.15–6.30(dd,1H) | |
| XXV | | | |
| XXVI | 5.22(s,2H) | 5.57–5.71(d,1H) | 6.83–7.57(m,8H) |
| XXVII | 5.07(s,2H) | 5.44–5.58(d,1H) | 6.85–7.55(m,16H) |
| | 5.12(s,2H) | 6.10–6.27(dd,1H) | |
| XXVIII | | | |
| XXIX | 5.21(s,2H) | 5.54–5.70(d,1H) | 6.93–7.63(m,8H) |
| XXX | 5.17(s,2H) | 5.53–5.68(d,1H) | 7.17–7.58(m,16H) |
| | 5.20(s,2H) | 6.20–6.37(dd,1H) | |
| XXXI | 5.17(s,2H) | 6.20–6.36(dd,1H) | 7.15–7.43(m,8H) |
| XXXII | 5.22(s,2H) | 5.57–5.70(d,1H) | 7.27–7.43(m,8H) |
| XXXIII | 5.19(s,2H) | 5.55–5.70(d,1H) | 7.23–7.83(m,16H) |
| | 5.23(s,2H) | 6.23–6.37(dd,1H) | |
| XXXIV | 5.08(s,2H) | 5.45–5.60(d,1H) | 3.73(s,6H) |
| | 5.12(s,2H) | 6.13–6.30(d,1H) | 6.77–7.46(m,16H) |
| XXXV | 5.13(s,2H) | 6.23–6.40(dd,1H) | 3.73(s,3H) |
| | | | 6.80–7.50(m,7H) |
| XXXVI | 5.15(s,2H) | 5.53–5.67(d,1H) | 7.17–7.53(m,7H) |
| | 5.18(s,2H) | 6.18–6.34(dd,1H) | |
| XXXVII | 5.19(s,2H) | 6.18–6.33(dd,1H) | 2.21(s,1H) |
| | | | 7.19–8.40(m,8H) |

In the normal use of the insecticidal and acaricidal esters of the present invention, the esters usually will not be employed free from admixture or dilution, but ordinarily will be used in a suitable formulated composition compatible with the method of application and comprising an insecticidally or acaricidally effective amount of substituted [1,1'-biphenyl]-3-ylmethyl 3-(2,2dihaloethenyl)-2,2-dimethylcyclopropanecarboxylate. The esters of this invention, like most pesticidal agents, may be blended with the agriculturally acceptable surface-active agents and carriers normally employed for facilitating the dispersion of active ingredients, recognizing the accepted fact that the formulation and mode of application of an insecticide or acaricide may affect the activity of the material. The present esters may be applied, for example, as sprays, dusts, or granules to the area where pest control is desired, the type of application varying of course with the pest and the environment. Thus, the esters of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the esters. The granule particles are relatively large, a diameter of about 400–2500 microns typically. The particles are either impregnated with the ester from solution or coated with the ester, adhesive sometimes being employed. Granules generally contain 1-15%, preferably 3-10%, active ingredient as the insecticidally effective amount.

Dusts are admixtures of the esters with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects and acarids contains 10 parts of (2,4-difluoro-[1,1'-biphenyl]-3-yl)methyl cis-3-(2,2-dichloroethenyl)-2,2-dimethylcyclopropanecarboxylate, 30 parts of bentonite clay, and 60 parts of talc.

The esters of the present invention may be made into liquid concentrates by dissolution or emulsification in suitable liquids and into solid concentrates by admixture with talc, clays, and other known solid carriers used in the pesticide art. The concentrates are compositions containing, as an insecticidally or acaricidally effective amount, about 5-50% substituted [1,1'-biphenyl]-3-ylmethyl 3-(2,2-dihaloethenyl)-2,2dimethylcyclopropanecarboxylate, such as (2'-methyl-[1,1'-biphenyl]-3-yl)methyl 3-(2,2-dichloroethenyl)-2,2-dimethylcyclopropanecarboxylate, and 95-50% inert material, which includes surface-active dispersing, emulsifying, and wetting agents. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects and acarids contains 1.5 parts each of sodium lignosulfonate and sodium laurylsulfate as wetting agents, 25 parts of (2'-fluoro-[1,1'-biphenyl]-3-yl)methyl 3-2,2-dichloroethenyl)-2,2-dimethylcyclopropanecarboxylate, and 72 parts of bentonite clay.

Useful liquid concentrates include the emulsifiable concentrates, which are homogeneous liquid or paste compositions readily dispersed in water or other liquid carriers. They may consist entirely of the ester with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1-15% by weight of the insecticidal and acaricidal composition.

Other useful formulations include simple solutions of the active ingredient in a solvent in which it is completely soluble at the desired concentration, such as acetone or other organic solvents.

An insecticidally or acaricidally effective amount of substituted [1,1'-biphenyl]-3-ylmethyl 3-(2,2-dihaloethenyl)-2,2-dimethylcyclopropanecarboxylate in an insecticidal and acaricidal composition diluted for application is normally in the range of about 0.001% to about 2% by weight. Many variations of spraying and dusting compositions known in the art may be used by substituting the esters of this invention into compositions known or apparent to the art.

The insecticidal and acaricidal compositions of this invention may be formulated with other active ingredients, including other insecticides, nematicides, acaricides, fungicides, plant growth regulators, fertilizers, etc. In using the compositions to control insects and acarids, it is only necessary that an insecticidally or acaricidally effective amount of substituted [1,1'-biphenyl]-3-ylmethyl 3-(2,2-dihaloethenyl)-2,2-dimethylcyclopropanecarboxylate be applied to the locus where control is desired. For most applications, as insecticidally or acaricidally effective amount of [1,1'-biphenyl]-3-ylmethyl 3-(2,2-dihaloethenyl)-2,2-dimethylcyclopropanecarboxylate will be about 75 to 4000 g per hectare, preferably 150 g to 3000 g per hectare.

The insecticidal and acaricidal activity of substituted [1,1'-biphenyl]-3-ylmethyl 3-(2,2-dihaloethenyl)-2,2-dimethylcyclopropanecarboxylates of Table 1 were evaluated as follows:

The ester (0.25 g) was dissolved in 20 ml of acetone, and this solution was dispersed in 180 ml of water containing one drop of isooctyl phenyl polyethoxyethanol. Aliquots of this solution, containing 1250 ppm ester, were diluted with appropriate amounts of water to provide test solutions containing lesser amounts of the active ingredient.

Test organisms and techniques were as follows: Activities against the Mexican bean beetle (*Epilachna varivestis* Muls.) and the southern armyworm (*Spodoptera eridania* [Cram.]) were evaluated by dipping the leaves of pinto bean plants into the test solution and, when the foliage had dried, infesting the leaves with the appropriate immature insects; activity against the pea aphid (*Acyrthosiphon pisum* [Harris]) was evaluated on broad bean plants whose leaves were dipped before infestation with adult aphids; activity against twospotted spider mites (*Tetranychus urticae* Koch) was evaluated on pinto bean plants whose leaves were dipped after infestation with adult mites; activities against the milkweed bug (*Oncopeltus fasciatus* [Dallas]) and the plum curculio (*Conotrachelus nenuphar* [Herbst]) were evaluated by spraying the test solutions into glass dishes or jars containing the adult insects. All organisms in the tests were maintained in a holding room at 80° F. and 50% relative humidity for an exposure period of 48 hours. At the end of this time, the dead and living insects or mites were counted, and the percent kill was calculated. Results of these tests are summarized in Table 3.

A number of the insecticidal and acaricidal compounds of this invention were also evaluated for efficacy in topical application to various insect species using techniques well known by those skilled in the art. For instance, the compound of Example XXXVII was so evaluated against southern armyworm larvae and other species; $LD_{50}=25$ nanograms/insect was determined from the southern armyworm data.

TABLE 3
ACTIVITY OF SUBSTITUTED [1,1'-BIPHENYL]-3-YLMETHYL 3-(2,2-DIHALOETHENYL)-2,2-DIMETHYLCYCLOPROPANECARBOXYLATES

| COMPOUND OF EX. | Conc. ppm. | Percent Kill Mexican Bean Beetle | Percent Kill Southern Armyworm |
|---|---|---|---|
| I | 1250 | 100 | 100 |
| II | 1250 | 100 | 100 |
| III | 1250 | 100 | 100 |
| IV | 1250 | 100 | 100 |
| V | 1250 | 100 | 100 |
| VI | 1250 | 100 | 100 |
| VII | 1250 | 100 | 100 |
| VIII | 1250 | 100 | 100 |
| IX | 1250 | 100 | 100 |
| X | 1250 | 100 | 100 |
| XI | 1250 | 100 | 100 |
| XII | 1250 | 100 | 100 |
| XIII | 1250 | 100 | 100 |
| XIV | 1250 | 100 | 100 |
| XV | 1250 | 100 | 100 |
| XVI | 1250 | 11 | 100 |
| XVII | 1250 | 100 | 100 |
| XVIII | 1250 | 100 | 100 |
| XIX | 512 | 100 | 100 |
| XX | 1250 | 94 | 100 |
| XXIII | 512 | 100 | 100 |
| XXIV | 1250 | 100 | 100 |
| XXVII | 1250 | 100 | 100 |
| XXX | 1250 | 100 | 100 |
| XXXIII | 1250 | 71 | 100 |
| XXXIV | 1250 | 100 | 100 |
| XXXVI | 512 | 100 | 100 |

| COMPOUND OF EX. | Pea Aphid | Twospotted Spider Mite | Milkweed Bug | Plum Curculio |
|---|---|---|---|---|
| I | 100 | 95.7 | 100 | 100 |
| II | 100 | 96.6 | 100 | |
| III | 100 | 0 | 100 | |
| IV | 100 | 21 | 95.4 | 29 |
| V | 100 | 61 | 100 | |
| VI | 100 | 96 | 100 | |
| VII | 100 | 8 | 100 | |
| VIII | 100 | 0 | 100 | 100 |
| IX | 100 | 76 | 50 | 0 |
| X | 100 | 0 | 100 | 15 |
| XI | 100 | 100 | 100 | |
| XII | 100 | 100 | 100 | |
| XIII | 100 | 100 | 100 | |
| XIV | 100 | 100 | 100 | 100 |
| XV | 100 | 0 | 95 | 65 |
| XVI | 100 | 0 | 99 | |
| XVII | 90 | 0 | 15 | |
| XVIII | 100 | 0 | 57 | |
| XIX | 100 | 0 | | |
| XX | 100 | 0 | 91 | 30 |
| XXIII | 100[a] | 94[a] | | |
| XXIV | 100 | 96.1 | 100 | |
| XXVII | 100 | 78 | 100 | |
| XXX | 100 | 74 | 100 | 100 |
| XXXIII | 100 | 0 | 100 | |

TABLE 3-continued
ACTIVITY OF SUBSTITUTED [1,1'-BIPHENYL]-3-YLMETHYL 3-(2,2-DIHALOETHENYL)-2,2-DIMETHYLCYCLOPROPANECARBOXYLATES

| | | | |
|---|---|---|---|
| XXXIV | 100 | 100 | 100 |
| XXXVI | 89 | 0 | |

[a]500 ppm

I claim:
1. A 3-(2,2-dihaloethenyl)-2,2-dimethylcyclopropanecarboxylate of the formula

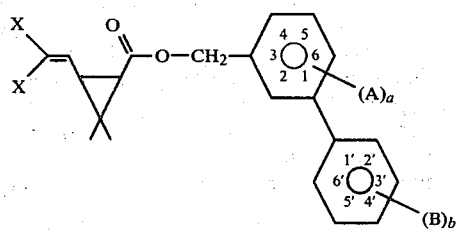

wherein X is chloro or bromo, and
b is 0, a is 1-4, and
when a is 1,
A is 2-, 4- or 6-halo, 5-fluoro, 2-lower alkyl, 2 trifluoromethyl, and
when a is 2,
A is fluoro, 2 and 4-chloro, or 2 and 4-bromo, and
when a is 3 or 4,
A is fluoro;
or
a is 0, b is 1-5, and
when b is 1,
B is halo, 2' or 3'-lower alkyl, 2' or 3'-trifluoromethyl, or 2' or 3'-lower alkoxy, and
when b is 2,
B is fluoro, 2' and 4'-chloro, 2' and 4'-bromo, and
when b is 3, 4 or 5,
B is fluoro.

2. A compound of claim 1 wherein X is chloro, lower alkyl is methyl or ethyl, and lower alkoxy is methoxy or ethoxy.

3. A compound of claim 1 wherein b is 0, a is 1, and A is halo.

4. (2Methyl-[1,1'-biphenyl]-3-yl)methyl 3-(2,2dichloroethenyl)-2,2-dimethylcyclopropanecarboxylate, a compound of claim 1.

5. A compound of claim 1 wherein b is 0, a is 2, and A is fluoro, 2 and 4-chloro, or 2 and 4-bromo.

6. (2,4-Dichloro-[1,1'-biphenyl]-3-yl)methyl cis-3-(2,2dichloroethenyl)-2,2-dimethylcylopropanecarboxylate, a compound of claim 5.

7. (2,4-Difluoro-[1,1'-biphenyl]-3-yl)methyl cis-3-(2,2-dichloroethenyl)-2,2-dimethylcyclopropanecarboxylate, a compound of claim 5.

8. A compound of claim 1 wherein b is 0, a is 1-4, and A is fluoro.

9. A compound of claim 1 wherein a is 0, b is 1, and B is fluoro, chloro, 2' or 3'-lower alkyl, 3'-trifluoromethyl, or 2'-lower alkoxy.

10. A compound of claim 9 wherein lower alkoxy is methoxy or ethoxy.

11. A compound of claim 9 wherein lower alkyl is methyl or ethyl.

12. (2'-Fluoro-[1,1'-biphenyl]-3-yl)methyl 3-(2,2-dichloroethenyl)-2,2-dimethylcyclopropanecarboxylate, a compound of claim 9.

13. (2'-Methyl-[1,1'-biphenyl]-3-yl)methyl 3-(2,2-dichloroethenyl)-2,2-dimethylcyclopropanecarboxylate, a compound of claim 9.

14. A compound of claim 1 wherein a is 1, b is 2, and B is fluoro or 2' and 4'-chloro.

15. A compound of claim 1 wherein a is 0, b is 1–5, and B is fluoro.

16. An insecticidal or acaricidal composition comprising an insecticidally or acaricidally effective amount of at least one compound of claim 1 in admixture with an agriculturally acceptable carrier.

17. A method of controlling insects or acarids which comprises applying to the locus where control is desired an insecticidally or acaricidally effective amount of at least one compound of claim 1.

UNITED STATES PATENT AND TRADEMARK OFFICE
CERTIFICATE OF CORRECTION

PATENT NO. : 4,214,004
DATED : July 22, 1980
INVENTOR(S) : Ernest L. Plummer

It is certified that error appears in the above—identified patent and that said Letters Patent is hereby corrected as shown below:

On the abstract page, under [*] Notice:, "Dec. 21, 1995" should read --Dec. 19, 1995--.
Col. 6, line 57, after "-3-methyl-", add --4-carbethoxy-2-cyclohexen-1-one. The crude product was distilled under reduced pressure to give 5-(2-fluorophenyl)-3-methyl-4-carbethoxy-2-cyclohexen-1-one (57.3 g); bp, 155-162°/1.2 mm.--.
Col. 12, Table 2, 2nd heading, "Methyl of Prep" should read --Meth of Prep--.
Col. 20, line 49, claim 4, "(2Methyl" should read --(2-Methyl--; "3-(2,2di" should read --3-(2,2-di- --.
line 55, claim 6, "(2,2dichloroethenyl)" should read --(2,2-dichloroethenyl)--; "dimethylcylopropanecarboxy-" should read --dimethylcyclopropanecarboxy- --.
Col. 21, line 1, claim 12, "3-(2,2di-" should read --3-(2,2-di- --; line 6, claim 13, "3-(2,2di-" should read --3-(2,2-di- --; line 9, claim 14, "a is 1" should read --a is 0--.

Signed and Sealed this

Twenty-fourth Day of February 1981

[SEAL]

Attest:

RENE D. TEGTMEYER

Attesting Officer    Acting Commissioner of Patents and Trademarks